United States Patent
Axford (10) Patent No.: US 8,173,437 B2
(45) Date of Patent: May 8, 2012

(54) RAPID SERUM SUGAR BIOMARKER ASSAY OF RHEUMATOID ARTHRITIS

(75) Inventor: John Axford, London (GB)

(73) Assignee: Mannatech, Incorporated, Coppell, TX (US)

( * ) Notice: Subject to any disclaimer, the term of this patent is extended or adjusted under 35 U.S.C. 154(b) by 54 days.

(21) Appl. No.: 11/450,500

(22) Filed: Jun. 9, 2006

(65) Prior Publication Data

US 2007/0087440 A1 Apr. 19, 2007

Related U.S. Application Data

(60) Provisional application No. 60/689,671, filed on Jun. 10, 2005.

(51) Int. Cl.
*G01N 33/00* (2006.01)
(52) U.S. Cl. ............................................. 436/94; 435/18
(58) Field of Classification Search ................... 436/94; 435/18
See application file for complete search history.

(56) References Cited

U.S. PATENT DOCUMENTS

2001/0023324 A1 9/2001 Pronovost et al.
2005/0112691 A1* 5/2005 Callewaert et al. ............ 435/7.1

FOREIGN PATENT DOCUMENTS

WO  WO 98/06418  * 2/1998

OTHER PUBLICATIONS

Axford John S., et al. Rheutatic disease differentiation using immunoglobulin G sugar printing by high density electrophoresis, J Rheumatol, 2003, 30, pp. 2540-2546.*
Alavi, A., et al., "Immunoglobulin G glycosylation and clinical outcome in rheumatoid arthritis during pregnancy," J Rheumatol 27 (2000) 1379-85.
Axford, J.S., et al., "Changes in normal glycosylation mechanisms in autoimmune rheumatic disease," J Clin Invest 89 (1992) 1021-31.
Axford, J.S., et al., "Rheumatic Disease Differentiation Using Immunoglobulin G Sugar Printing by High Density Electrophoresis," J. Rheumatol 30 . (2003) 2540-46.
Bond, A., et al., "A Detailed Lectin Analysis of IgG Glycosylation, Demonstrating Disease Specific Changes in Terminal Galactose and N-acetylglucosamine," J Autoimmun 10 (1997) 77-85.
Craig, R., and A. Atkinson, Jr. "D-xylose testing: a review," Gastroenterology (1988) 95:223-231.
Watson, M., et al., "Sugar printing rheumatic diseases: A potential method for disease differentiation using immunoglobulin G oligosaccharides," Arthritis Rheum 42 (1999) 1682-90.

* cited by examiner

*Primary Examiner* — Christine T Mui
(74) *Attorney, Agent, or Firm* — Edwin S. Flores; Chainey P. Singleton; Chalker Flores, LLP (57) ABSTRACT

The present invention includes compositions, methods, kits and diagnostics for biosugar profiling of biological samples from a patient suspected of having a disease associated with changes in the biosugar profile. The biosugar profile from the patient sample is compared to a healthy biosugar profile from the same type of biological sample to evaluate disease potential and progression.

20 Claims, 5 Drawing Sheets

RAPID SERUM SUGAR BIOMARKER ASSAY OF RHEUMATOID ARTHRITIS

TECHNICAL FIELD OF THE INVENTION

This application claims priority to U.S. Provisional Application Ser. No. 60/689,671, filed Jun. 10, 2005, the entire contents of which are incorporated by reference.

The present invention relates in general to the field of biomarker assays and, more particularly, to systems, methods and kits for the rapid determination of sugar biomarkers from bodily fluids and tissues.

BACKGROUND OF THE INVENTION

Without limiting the scope of the invention, its background is described in connection with biomarkers.

Despite advances in the fields of genomics and proteomics, a need remains for diagnostic methods and therapeutic regimens to address a large number of diseases. The fields of genomics and proteomics have served as the starting point for biological investigation as a result of the relative simplicity of their underlying subunits. In the case of genomics, scientists merely had to contend with a basic four (4) letter, linear deoxyribonucleic acid alphabet. As such, the genetic code and its determination as part of the human and other genome projects has led to vast amounts of sequence information. For proteomics, the level of complexity increases to about 20 amino acids, which are also generally linear and that are based on the underlying genetic code. Proteins have the added complexity of three-dimensional folding, with great strides in the fields of three-dimensional modeling, nuclear magnetic resonance and X-ray crystallography providing valuable tools and insight into protein structures and interaction.

Despite the sequencing of the entire human genome, large-scale gene mining operations and extensive research into the underlying causes of disease, little work has been conducted in the area of post-translational modification. The general availability of research tools may be the reason why the study of post-translational modifications has lagged behind that of the genetic code and protein expression. While the tools for determining the genetic code have been widely available for 30 years, wide spread training and availability of tools for the in-depth study of post-translational modifications, such as glycosylation, has not been generally available. The complexity of studies into post-translational modification is greatly increased by the vast numbers and complexity of the subunits, branching and even secondary modifications.

Specific examples of inventions in the general field of post-translational, glycosylation, modifications include, e.g., U.S. Pat. No. 4,659,659 issued to Dwek, et al., for a diagnostic method for diseases having an arthritic component. This patent teaches a method for the diagnosis of diseases having an arthritic component (such as rheumatoid arthritis and osteoarthritis) by determining the deficiency of galactose in a sample of the patient's blood serum or plasma, or synovial fluid, or an immunoglobulin (Ig) component or fragment thereof in comparison with the corresponding normal values of galactose. More particularly, these inventors teach a method for the diagnosis of rheumatoid arthritis or osteoarthritis as a sole syndrome or as a component of other rheumatic diseases by determining the deficiency of a single post-translational modification of a single saccharide, namely, the outer-arm galactosylation of an immunoglobulin G (IgG) component or fragment thereof in a patient's blood serum or plasma or synovial fluid by assaying for the incidence of non-reducing terminal outer arm N-acetylglucosamine residues of the IgG component or fragment and comparing with corresponding normal control values.

Another example is U.S. Reissue Pat. No. RE 35,417, issued to Rademacher, et al., which teaches oligosaccharide sequencing. More particularly, a method of oligosaccharide sequencing is taught in which the components are determined essentially simultaneously by: placing an identifying label on the reducing terminal residue of the oligosaccharide to be sequenced; dividing the oligosaccharide into a plurality of separate portions of known integer amounts; treating each the portion with a different reagent mix to thereby provide a series of reaction mixtures; pooling known integer amounts of the products from each separate reaction mixture to give a product pool; performing an analysis on the product pool which measures the molar proportions of the reaction products, and reconstructing or identifying the starting oligosaccharide from the molar prevalence of the reaction products. Again, this method relies on the sequencing of individual saccharides and is limited to a basic observational determination of the sequence without taking into account branching or other modifications.

United States Patent Application No. 20040152130, filed by Gilmore, et al., is said to teach a method for determining secondary modifications of molecules using arrays. The application provides methods for simultaneous detection of multiple secondary modifications, such as "post-translational modifications," of target molecules, e.g., polypeptides, using an "array" format. More particularly, the method detects a secondary modification of a target molecule by: providing an array with a plurality of biosites, each biosite including a plurality of capture probes immobilized to a substrate surface; providing the target molecule; providing a detection probe capable of binding to a capture probe-bound target molecule; and, contacting the target molecule with the array and the detection probe with the target molecule and detecting which biosite comprises a bound target molecule and detection probe. Again, basic observations of the possible structure of the modification are observed without any further analysis or correlation.

Finally, United States Patent Application No. 20040067541, filed by Dwek, Miriam Victorine, et al., is directed to an assay method for the detection of detectable changes in the levels of fucosylation in Prostate Specific Antigen. An assay is taught in which a sample from a prostate suspected of being cancerous is obtained and cells and cell debris from the sample are assayed for the presence of a glycosylated protein uniquely associated with the prostate, namely, fucosylation thereof. The levels of fucosylation are compared with a standard control value indicative of a male human subject having a normal, non-cancerous prostate gland. A level of fucosylation in the sample that is statistically significantly greater than that of the control is taken as indicative of the cancerous condition.

SUMMARY OF THE INVENTION

More particularly, the present invention includes diagnostic systems and methods that compare the biosugar profile of a biological sample of a patient suspected of having a disease associated with changes in the biosugar profile to a healthy biosugar profile from the same type of biological sample. Non-limiting examples of biological samples include: serum, blood, plasma, urine, saliva, peritoneal, stool, mucus, tears, sweat, synovial fluid, biopsies or cerebrospinal fluid. The patient may be a mammal suspected of having an auto-inflammatory disease, an auto-immune disease, a metabolic disease, a neurological disease, an infectious disease or combinations thereof. The biosugar profile may be determined using high density electrophoresis, e.g., Fluorophore Assisted Carbohydrate Electrophoresis (FACE), high performance anion-exchange chromatography (HPAEC), with pulsed amperometric detection (HPAEC-PAD) and/or fluorescent detection system, matrix-assisted laser desorption/ ionization mass spectroscopy time of flight—mass spectrometry (MALDI-TOF MS), enzyme-linked immunosorbent/ lectin based assay and/or combinations thereof.

Yet another aspect of the present invention are formulations and methods that may be provided to a patient in need thereof, a formulation that modifies the biosugar profile of the patient. Examples of formulations include, e.g., dietary supplements for the diet of a patient with one or more saccharides in a nutritionally effective amount selected from galactose, galactosamine, glucosamine, glucose, mannose, acetylated-mannose, N-acetylneuraminic acid, fucose, N-acetylgalactosamine, N-acetylglucosamine, xylose and mixtures or combinations thereof based on the biosugar profile. Yet another example of supplementation may include one or more of the following saccharides in a nutritionally effective amount obtained from: gum tragacanth, guar gum, grain flour, rice flour, sugar cane, beet sugar, potato, milk, agar, algin, locust bean gum, psyllium, karaya gum, seed gums, Larch tree extract, aloe vera extract, gum ghatti, starch, cellulose, degraded cellulose, fructose, high fructose corn syrup, pectin, chitin, acacia, gum arabic, alginic acid, carrageenan, dextran, xanthan gum, chondroitin sulfate, sucrose, acetylated polymannose, maltose, glucan, lentinan, mannan, levan, hemicellulose, inulin, fructan, lactose and mixtures or combinations thereof. In addition to these saccharides, the formulation may include one or more nutritional supplements in a nutritionally effective amount selected from anti-oxidants, vitamins, minerals, amino acids, nucleic acids, saccharides, herbal extracts, mixtures and combinations thereof.

As such, the method of the present invention may include not only the detection of changes to the biosugar profile of one or more proteins, peptides, lipids, polysaccharides and the like, but also, the step of administering to the patient a nutritionally effective amount of a formulation that modifies the biosugar profile orally, intravenously, intramuscularly, intraperitoneally, subcutaneously, by intranasal instillation, by application to mucous membranes, or by instillation into hollow organ walls or newly vascularized blood vessels. The patient may be suspected of having an inflammatory disease selected from the group consisting of transplantation rejection, nephritis, asthma, respiratory distress syndrome, gastritis, rheumatoid diseases, sepsis, thrombosis, autoimmune diseases, and coronary disease. Alternatively or conjunctively, the patient may be suspected of exhibiting or having a transplantation rejection, a renal allograft rejection, a cardiac allograft rejection, a transplantation-associated vasculopathy, a nephritis, an acute glomerulonephritis, lupus nephritis, and tubulointerstitial nephritis, an asthma, an allergic asthma, a respiratory distress syndrome, a gastritis, a rheumatoid disease selected from the group consisting of lupus and arthritis, a vasculitis, a diabetes, a sepsis, a thrombosis, a coronary artery disease selected from the group consisting of restenosis after angioplasty, restenosis after by-pass surgery, ischemia, tuberculosis or an inflammatory bowel disease.

The present invention also includes systems, compositions and methods of determining or detecting a deficiency in one or more essential saccharides by obtaining a biological sample from a mammal suspected of having a deficiency in one or more essential saccharides and determining a biosugar profile of the biological sample. The deficiency may be overcome with one or more essential saccharides in determined and an essential sugar supplement is designed to supplement the modified biosugar profile. The biological sample is a serum, a blood, a plasma, a urine, a saliva, synovial fluid, a peritoneal, a stool, a mucus, a tear, a sweat, a biopsy or a cerebrospinal fluid sample. The method may also include the step of administering to the mammal a nutritionally effective amount of a formulation that modifies the biosugar profile orally, intravenously, intramuscularly, intraperitoneally, subcutaneously, by intranasal instillation, by application to mucous membranes, or by instillation into hollow organ walls or newly vascularized blood vessels. Other examples of conditions include: transplant rejection, nephritis, asthma, respiratory distress syndrome, gastritis, rheumatoid diseases, sepsis, thrombosis, autoimmune diseases, and coronary disease.

The present invention may be provided in the form of a kit that may include, e.g., a container adapted to stably maintain a biosugar biological fluid sample and instructions for collection and preservation of the biosugar sample. The kit may be for home, clinic, hospital or other use and may be reusable or disposable. In one embodiment, the biological sample is exposed to a biosugar marker test strip adapted to visualize the presence or absence of specific individual saccharides, disaccharides, polysaccharides or combinations and mixtures thereof. The biosugar marker test strip may be specific for, e.g., an auto-inflammatory disease, an auto-immune disease, a metabolic disease, an infectious disease or combinations thereof. Examples of biological samples may include a serum, a blood, a plasma, a urine, a saliva, synovial fluid, a peritoneal, a stool, a mucus, a tear, a sweat, a biopsy or a cerebrospinal fluid sample, again, depending on the nature of the condition, location of isolation, availability of appropriate facilities for sample isolation, the need for quantitative and/or qualitative analysis and the like. The strip may detect the presence or absence of one or more essential saccharides or oligosaccharides and/or instructions on formulations that supplement the one or more missing essential saccharides.

BRIEF DESCRIPTION OF THE DRAWINGS

For a more complete understanding of the features and advantages of the present invention, reference is now made to the detailed description of the invention along with the accompanying figures and in which.

DETAILED DESCRIPTION OF THE INVENTION

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. The terminology herein is used to describe specific embodiments of the invention, but their usage does not delimit the invention, except as outlined in the claims.

The term "or combinations thereof" as used herein refers to all permutations and combinations of the listed items preceding the term. For example, "A, B, C, or combinations thereof" is intended to include at least one of, A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, MB, BBC, AAABCCCC, CBBAAA, CABABB, and so forth. The skilled artisan will understand that typically there is no limit on the number of items or terms in any combination, unless otherwise apparent from the context.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

As used herein, the term "biosugar" is used to describe mono, di, tri and polysaccharides that are linear, branched, etc. and that are found free or attached to, e.g., proteins, lipids, other carbohydrates, in biological samples.

As used herein, the term "essential saccharides," is used to define the monosaccharides commonly found in the oligosaccharide chains of cellular glycoproteins and which may not be readily available through diet or biochemical manufacture in the human body (see, e.g., Harper's Biochemistry (Murray et al., 1996)(listing eight) and Principles of Biochemistry, Vol II (Zubay, et al., 1995)(listing eleven). While over 200 monosaccharides have been found in nature, these eleven are believed to be important toward maintaining good health in mammals: galactose, glucose, mannose, N-acetylneuraminic acid, fucose, N-acetylgalactosamine, N-acetylglucosamine, xylose, iduronic acid, arabinose and glucuronic acid. The structures of these carbohydrates are well-known (see, e.g., Stryer's Biochemistry (Stryer, 1995) and the Merck Index, 12th Edition, 1996).

As used herein, the terms "glyconutritional" or "glyconutrient" refer to complex carbohydrates or saccharides or simple sugars that are synthesized in nature and are necessary for the biochemical synthesis of various classes of communication and signal molecules that may be free in interstitial cellular fluids, active in cell to cell communication (i.e., cytokines, growth factors, etc.), or constitute the molecular configuration comprising foci of highly specific molecular activity of cell membranes (i.e., receptor sites, ion-transport channels, antigenic identification, and the like).

As used herein, the terms "phytonutritional" or "phytonutrient" refer to naturally synthesized molecules found only in plants that are produced to protect the plant's cells. Phytonutrients primarily have antioxidant, free-radical scavenger and vital micronutrient activity. These molecules, supplied through dietary supplementation, are found in mature plant tissues, and are most concentrated in seed coats and fruiting tissues surrounding the seed. In. mammalian tissues, these molecules, when supplied in the diet, are active in optimizing the biochemistry, immunology and physiology in the cellular micro-environment.

As used herein, the terms "plant extract" and "herbal extract" are used interchangeably to refer to phytochemicals that are produced in plant tissues and that can be extracted by water, polar, or petroleum solvents, and that have some degree of beneficial health or therapeutic activity. Most herbal agents can be toxic, especially when concentrated, but are generally safe when utilized in their more traditional manner in teas and poultices as a "folk medicinal for the treatment of disease and promotion of good health." As used herein, the term "herbal body-toning agent" refers to substances that have been observed by the inventors to reduce and reverse elastic tissue and collagen fiber damage caused by aging or sun-damage as evidenced by a restoration of skin turgor and elasticity which effectively reduces or eliminates wrinkles, sagging, hyperpigmentation and reversal of other undesirable elements of lost cosmetic appearance.

The carbohydrates included in the dietary supplement of the invention are available from a wide variety of natural and synthetic sources such as shrubs, trees, plants, yeasts, fungi, molds, gums, resins, starch and cellulose derivatives and natural mucin sources. Specifically, some of the natural sources include: (a) shrub or tree exudates which contain acacia, karaya, tragacanth, or ghatti; (b) marine gums which include agar, algin, or carrageenan; (c) seed gums which include guar, locust bean, or psyllium; (d) plant extracts which contain pectins or acetylated polymannose; (e) starch and cellulose derivatives such as hetastarch, carboxymethylcellulose, ethylcellulose, hydroxypropyl methylcellulose, methylcellulose, oxidized cellulose; and microbial gums which contain dextrans, xanthan. However, it should be recognized that the composition of the invention is not intended to be limited by the source from which the respective carbohydrates are obtained.

The saccharides of the invention can be found in nature as mono-, oligo- and/or polysaccharides. Thus, the compositions of the invention can contain the saccharides in their monomeric, oligomeric and/or polymeric forms. For a list of known natural sources for the saccharides and their uses, please refer to U.S. Patent Application No. US2003072770, relevant portions incorporated herein by reference.

As used herein, the term "carbohydrate" is used interchangeably with the terms "saccharide," "polysaccharide," "oligosaccharide" and "sugar" the definitions of which are well known to those skilled in the art of carbohydrate chemistry. Although the compositions of the invention are intended to include at least two or more essential saccharides, it should be noted that the saccharides can be in the form of mono-, oligo- and/or polysaccharides, e.g., a composition that includes gum tragacanth and guar gum will be considered as containing galacturonic acid, sialic acid, mannose and galactose. Therefore, by controlling the amount of particular gums in a given dietary supplement, one can control the amount of the respective saccharides in the dietary supplement.

Although the present invention includes the above cited eleven essential saccharides, it should be noted that other saccharides, nutritional compounds or biologically active or inert compounds may be included in the dietary supplement of the invention. Such other nutritional compounds include any one or more of phytonutrients, dioscorea complex, plant extracts, herbal extracts, plant parts, herbal components, vitamins or minerals. These nutritional compounds can be added to the dietary supplement of the invention, or they can be provided separately to a mammal being administered the dietary supplement. For example, a person receiving the glyconutrient-containing dosage form of the invention can also receive a phytonutrient in either the same or a separate dosage form. Inert compounds can include flavors, fillers, lubricants, buffers, gels, binders, excipients, carriers and/or other such compounds that facilitate the formulation or administration of the inventive dietary supplement. All of the glyconutrient containing dietary supplement compositions of the invention, even those containing additional compounds, agents or other substances, can be obtained directly from Mannatech, Inc. (Coppell, Tex.).

As used herein the terms, "long-chain saccharides" and "long-chain polysaccharides" are used to describe those chains of saccharides that have two or more saccharides that are capable of intrachain hydrogen binding. For example, in U.S. Pat. No. 4,735,935, relevant portions incorporated herein by reference, teaches the methods of isolation of long-chain polysaccharides from Aloe vera, in which the precipitated, lyophilized long-chain polysaccharides have from 2 to about 50,000 monomers per chain. The long-chain polysaccharides can be isolated from a variety of plant and animal sources, as taught and disclosed herein. Isolating and purifying the long-chain polysaccharides of the present invention, and even isolating specific chain lengths or combinations thereof may be obtained by, e.g., hydrolyzing the long-chain polysaccharides, bulk isolation of specific lengths of longchain polysaccharides, polymerizing longer long-chain polysaccharides, selecting combinations of shorter and longer long-chain polysaccharides, separating the long-chain polysaccharides by, e.g., electroporation, FPLC, HPLC, size-exclusion, size-exclusion chromatography, precipitation and the like.

As used herein the term "nutritionally effective amount" is used to define the amount that will provide a beneficial nutritional effect or response in a mammal. For example, as nutritional response to vitamin- and mineral-containing dietary supplements varies from mammal to mammal, it should be understood that nutritionally effective amounts of the vitamins and minerals will vary, respectively. Likewise, the lack of an essential amino acid, vitamin-C, iron, iodine, vitamins, minerals, carbohydrates, lipids and the like are known to affect physiological and cellular functions. A nutritionally effective amount of the anti-oxidants and saccharides disclosed herein serve to preserve and/or elevate the levels of these critical nutrients in the diet of, e.g., a human that seeks to maintain or augment their diet for these nutritional supplements. Thus, while one mammal may require a particular profile of vitamins and minerals present in defined amounts, another mammal may require the same particular profile of vitamins and minerals present in different defined amounts.

The present invention was developed to detect the presence of sugar print biomarkers within the body that may be associated with health and disease. The invention may be used to determine and quantitate the long-term effects of dietary supplementation with glyconutrients. In order to determine and quantitate these effects of glyconutyrients, the present invention was designed to provide a rapid, accurate and easy to carry out sugar print biomarker detection systems, methods, individual use strips and kits. Using the technology and methods disclosed herein, both simple and complex sugar patterns and effects can be measured and tracked. With better tracking and evaluation techniques physicians and clients will be better able to distinguish between health and disease and to monitor sugar print biomarker changes as a result of dietary supplementation with glyconutrients.

The present invention used among other detection assays, High Density Sugar Electrophoresis, Fluorescent tagging, High Performance Anion-Exchange Chromatography with Pulsed Amperometric and/or fluorescent Detection and Mass Spectrometry as well as Lectin based assays to determine if a wide arrays of Glycoprotein sugars can be efficiently detected in serum, urine and saliva and if there are detectable disease differences at the micro and macroscale.

Using the techniques and tools provided herein, individual users, researchers and physicians will be able to monitor the immediate status, short- and long-term changes and, potentially, provide predictive information regarding disease states. The tests developed and taught herein provide confirmation of the practicality of serum, saliva and urine sugar analysis and provide a cross-sectional analysis in health and disease. In operation, the sugar print biomarker detection systems, methods, strips and kits will be available to both the physician and patient to track micro and macro-scale changes in sugar biomarkers and provide, e.g., sugar bioprints that may be used to detect and track current and future correlations with disease states.

High Density Electrophoresis. A novel high density electrophoresis-based imaging system [1] was developed that essentially involves release of sugars from IgG using the endoglycosidase peptide-N-glycosidase F, fluorophore-labelling the sugars with 2-amino benzamide acid, resolving a known total quantity of the sugar on a polyacrylamide based gel, and analyzing the sugar bands by optical density with a GAS7000 (UVI-Pro, UVItec, Cambridge, UK) gel scanning system (FIG. 1) to determine relative quantities of each sugar.

Sugar Analysis in Disease: Rheumatic Disease. Initial studies were used to demonstrate the use of micro- and macro-scale techniques and methods to determine whether immunoglobulin G (IgG) sugar printing using high density electrophoresis can be a diagnostic and prognostic test to rapidly differentiate early rheumatoid arthritis [2-5].

Sugar Analysis in Disease: Inflammatory Bowel Disease. The diagnosis of Inflammatory Bowel Disease (IBD) is usually made using both clinical and pathological parameters. However, in approximately 15% of cases, no clear diagnosis can be made even after surgery has been carried out. Such cases are termed indeterminate colitis. Problems arise when reconstructive surgery appropriate for ulcerative colitis (UC) has been carried out on patients with masked Crohn's disease (CD); such patients have a 50% risk of failure of their pouches. As yet, no specific biomarker exists to differentiate between the two types of IBD.

IgG agalactosylation has been demonstrated in Crohn's disease [3, 6]. The degree of agalactosylation in CD has been shown to associated with the acute phase response; it correlates with the level of C-reactive protein [6] Interestingly, the degree of IgG agalactosylation in CD is in par with those found in patients with rheumatoid arthritis and has been shown to exhibit a similar reciprocal galactose:N-acetylglucosamine relationship to that of RA [3].

Sugar Analysis in Disease: Infections Diseases. Decreases in IgG galactose content has been reported in a number of infectious diseases: Mycobacterium tuberculosis [7, 8], Mycobacterium lepri [9] and Borrelia burgdorferi [10]. Interestingly, in the latter two diseases the reduction in galactose occurs at certain disease stages only, erythema nodosum leprosum and chronic arthritis respectively. IgG agalactosylation has also been noted in Takayasu's arteritis which is also linked to mycobacterioses [11] and in patients with infective endocarditis [3]. Animal studies have also demonstrated links with the arthritic phase of lentiviral infection [12].

High performance anion-exchange chromatography (HPAEC). The use of HPAEC has facilitated the quantification of monosaccharides without prior derivatization [13]. HPAEC is a widely used, powerful, technique for the rapid and direct analysis of carbohydrates. It takes advantage of the weakly acidic nature of carbohydrates and the highly selective separation of these at high pH using a strong Anion-Exchange Matrix. It allows for the separation of glycoprotein derived oligosaccharides on the basis of charge (FIGS. 3 and 4), but can also resolve oligosaccharides with the same charge according to: (1) size; (2) sugar composition; and/or (3) linkage.

Figure 1:
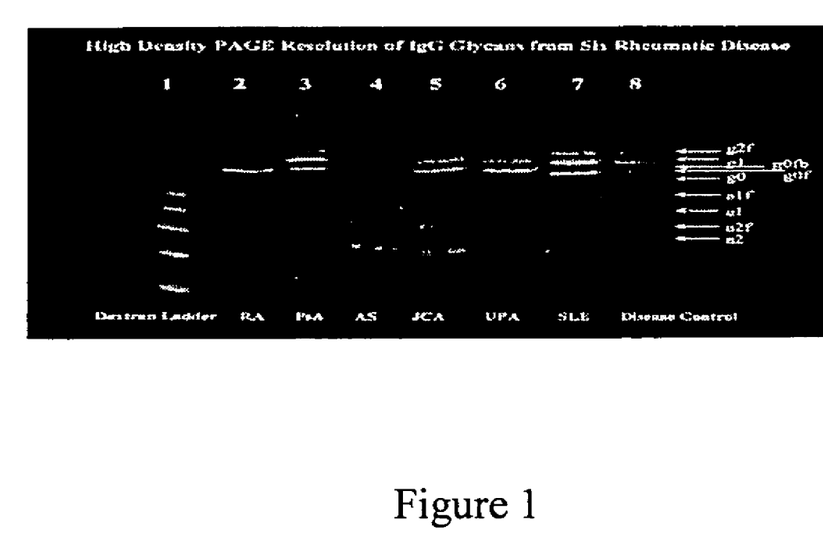
FIG. 1 is a gel showing the resolution of IgG N-glycans from 6 rheumatic diseases using Fluorophore Assisted Carbohydrate Electrophoresis (FACE). Lane 1; Homopolymer glucose ladder, Lane 2; rheumatoid arthritis (RA), Lane 3; psoriatic arthritis (PsA), Lane 4; ankylosing spondylitis (AS), Lane 5; juvenile chronic arthritis (JCA), Lane 6; undifferentiated polyarthritis arthritis (UPA), Lane 7; systemic lupus erythematosus (SLE) and Lane 8; osteoarthritis disease control. Identity of glycan bands is shown on the right.

As demonstrated herein, the sugars may be characterized by either: (1) co-elution with standards; and/or (2) retention time comparisons. FIG. 1 is a high density polyacrylamide gel electrophoresis that shows the macro-scale resolution of IgG N-glycans from 6 rheumatic diseases. Two aminobenzoic acid-labelled IgG N-glycans resolved on 30% polyacrylamide gels with Tris-glycine running buffer. Lane 1; Homopolymer glucose ladder, Lane 2; rheumatoid arthritis (RA), Lane 3; psoriatic arthritis (PsA), Lane 4; ankylosing spondylitis (AS), Lane 5; juvenile chronic arthritis (JCA), Lane 6; undifferentiated polyarthritis arthritis (UPA), Lane 7; systemic lupus erythematosus (SLE) and Lane 8; osteoarthritis disease control. Identity of glycan bands is shown on the right.

IgG sugar printing was found to be effective in differentiation of rheumatic diseases and can differentiate early RA and established RA from each other and from other rheumatic diseases (FIG. 1); and hence may constitute a relatively rapid diagnostic and prognostic test for patients presenting with arthritis [1].

Figure 2:
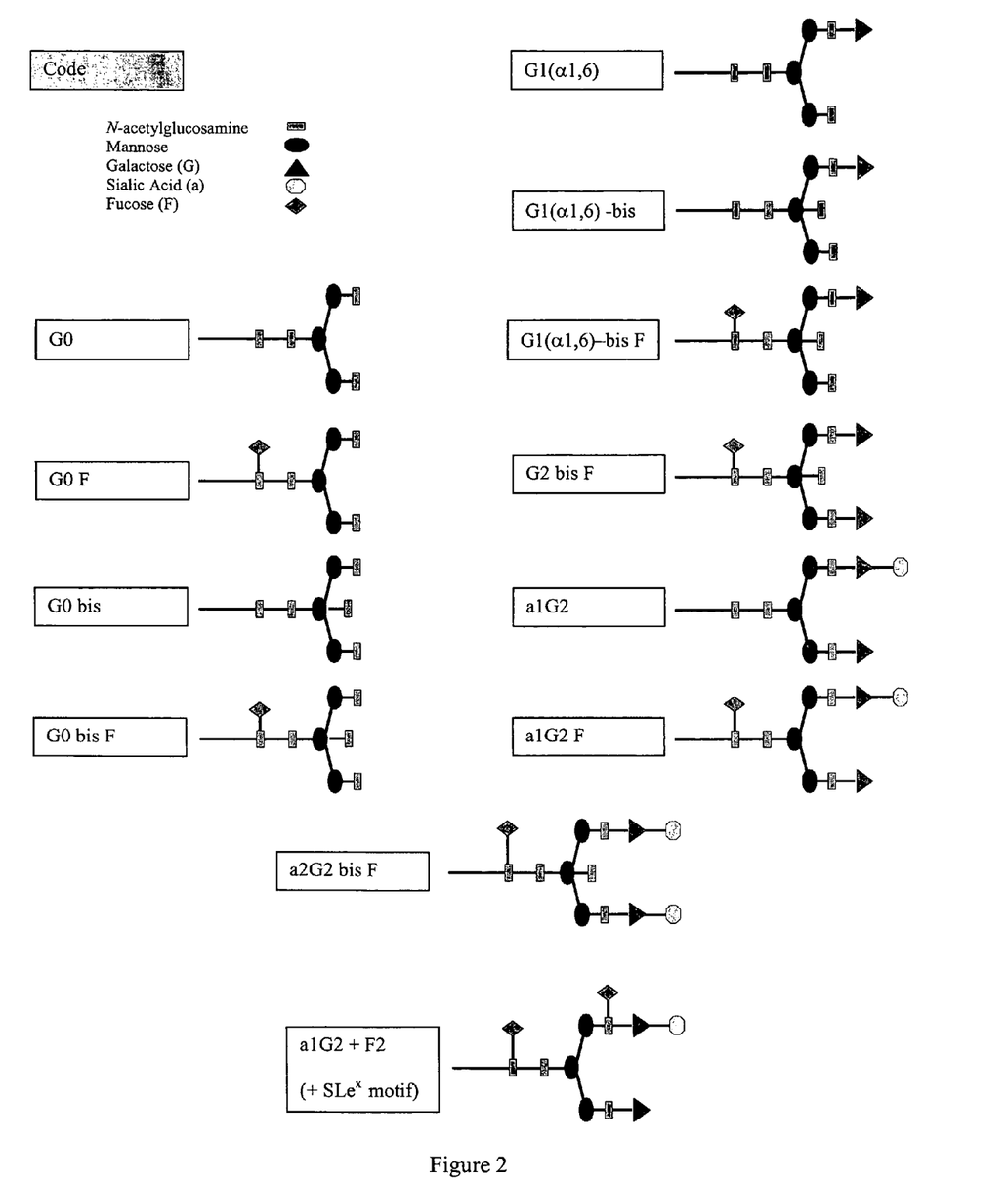
FIG. 2 Pictogram representation of some of the >30 complex neutral and sialylated N-linked oligosaccharides associated with the RA and control serum glycoproteins; Glycans are designated by G0, G1 and G2; according to the number of terminal galactose residues, followed by bis (bisecting N-acetylglucosamine and/F (Fucose), and a1 and/or a2; according to the number of terminal sialic acid residues.

FIG. 2 is a summary of structures of some of the >30 complex neutral and sialylated N-linked oligosaccharides associated with the RA and control serum glycoproteins; Glycans are designated by G0, G1 and G2; according to the number of terminal galactose residues, followed by bis (bisecting N-acetylglucosamine and/F (Fucose), and a1 and or a2; according to the number of terminal sialic acid residues.

Using a combination of six exoglycosidases, terminal monosaccharides can be released from oligosaccharides for analysis. Using the Dionex CarboPac PA1 and PA 100 columns, these released monosaccharides and the remaining oligosaccharides can be separated and identified using HPAEC-PAD. These oligosaccharides also elute in a predictable manner and several empirical rules can be used to predict the relative times at which they elute. In every digestion, the appearance of the oligo and monosaccharide products can be monitored directly by injecting the digestion into the analytical system. Identities of these products can be confirmed by a comparison with appropriate standards.

Pulsed Amperometric Detection (PAD). Pulsed amperometric detection provides sensitive and specific detection, eliminating interference from most non-carbohydrate matrix components. The pulsed amperometry exhibits excellent signal-to-noise ratios and permits detection of carbohydrates via the electrical current generated by their oxidation at the surface of a gold electrode.

Thus, the high resolution of the CarboPac columns coupled with pulsed amperometric detection allows structural information of N-linked glycans to be obtained without extensive sample clean up. The eluted oligosaccharides can undergo further, more detailed, structural analysis by Mass Spectrometry (FIG. 4) and NMR [14].

Figure 5:
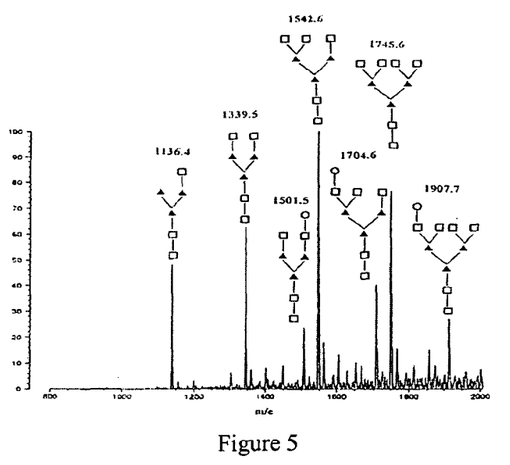
FIG. 5 is a chromatograph that shows the separation of neutral oligosaccharides by mass spectrometry: square=N acetyiglucosamine; triangle=mannose; circle=galactose.

FIG. 5 is a graph that shows the separation of neutral oligosaccharides by mass spectrometry: square=N acetylglucosamine; triangle=Mannose; circle=Galactose.

Figure 3:
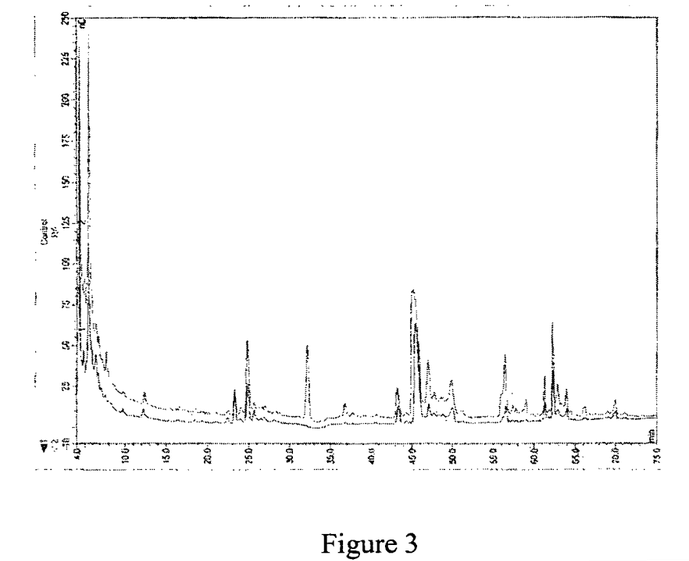
FIG. 3 is an HPAEC-PAD analysis of N-glycans from: (i) a normal healthy serum in blue, and (ii) a RA serum in green; the y and x axis represent detector response (nC) and retention time (min) respectively.
Figure 4:
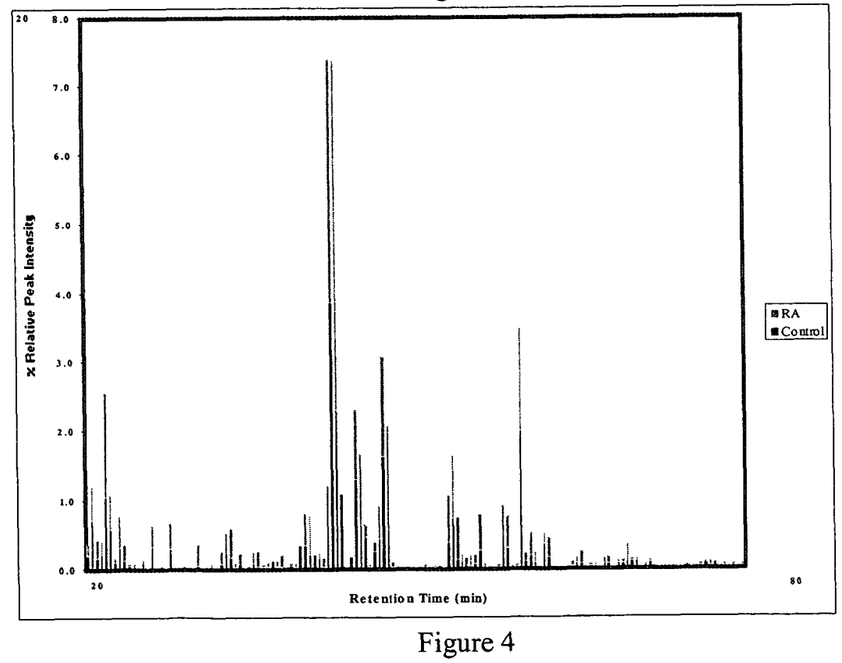
FIG. 4 is a comparative analysis of the serum oligosaccharide profile for the RA (n=10; green) and healthy controls (n=10; blue) using HPAEC-PAD; indicating changes in the neutral, mono-, di, tri and tetra sialylated structures (retention time 20-32, 40-50, 52-60, and >60 respectively)

Analysis of serum sugars. Initial studies were carried out to determine whether high density electrophoresis [17], HPAEC-PAD (FIG. 5) and MALDI-TOF MS (FIGS. 6 and 7) can be used to detect RA specific sugar changes in whole serum. In the initial study, data were generated to cover the entire range of possible N-oligosaccharides associated with serum glycoproteins (FIG. 3). FIG. 3 is a graph that compares HPAEC-PAD analysis of N-linked oligosaccharides enzymatically cleaved from normal healthy serum and RA serum, glycoproteins. The results indicate possible differences in the profile of the following oligosaccharides: (i) Neutral structures [10-32 min on the x-axis]; (ii) Monosialylated structures [33-42 min]; (iii) Disialylated bi- and tri-antennary structures [47-60 min].

The regions of interest in the HPAEC-PAD sugar profiles can be analyzed in greater detail by setting and running the system under conditions that are optimum for greater separation of a given type of oligosaccharide family, e.g., neutral oligosaccharides. This would enable us to focus-in on the different regions and to obtain a clearer picture of the possible disease associated differences.

These studies demonstrate that both the HPAEC-PAD (FIGS. 3 and 4) and MALDI-TOF (FIGS. 6 and 7) can be efficiently utilized to provide complete sugar profiles and raise the possibility that there may be glycoproteins other than IgG undergoing RA specific sugar variation. In addition, it raises the possibility of the presence of disease associated sugar print biomarkers as determinants of health and disease.

Figure 6:
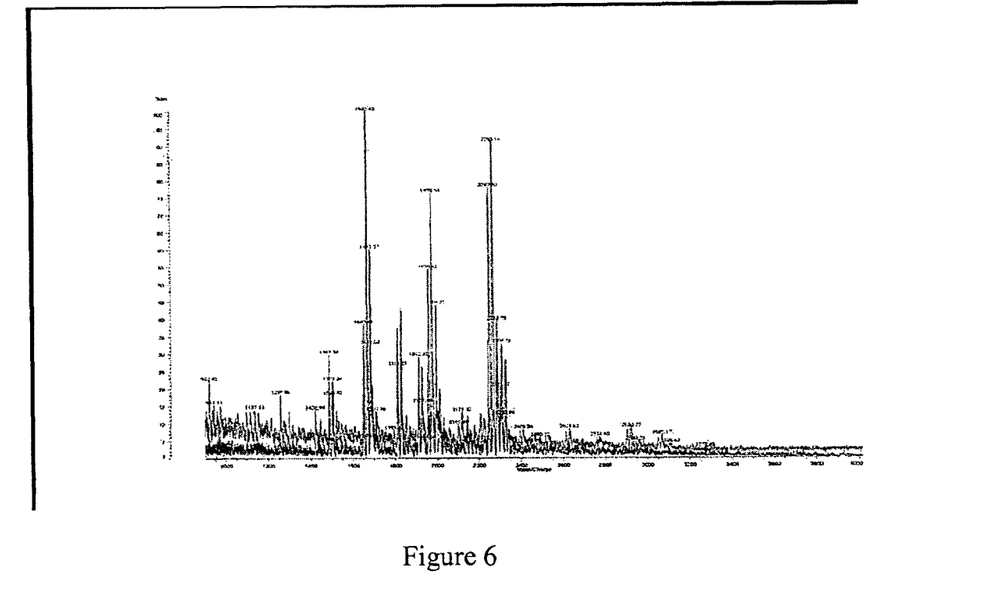
FIG. 6 MALDI-TOF MS spectrum of one RA (green) and one healthy control (blue); The y and x axis represent percent (%) intensity and Mass/charge ratio (m/z) respectively.

FIG. 6 is a graph that shows the MALDI-TOF MS Profile of N-linked Sugars Derived from normal serum; and serum of a patient with RA.

Figure 7:
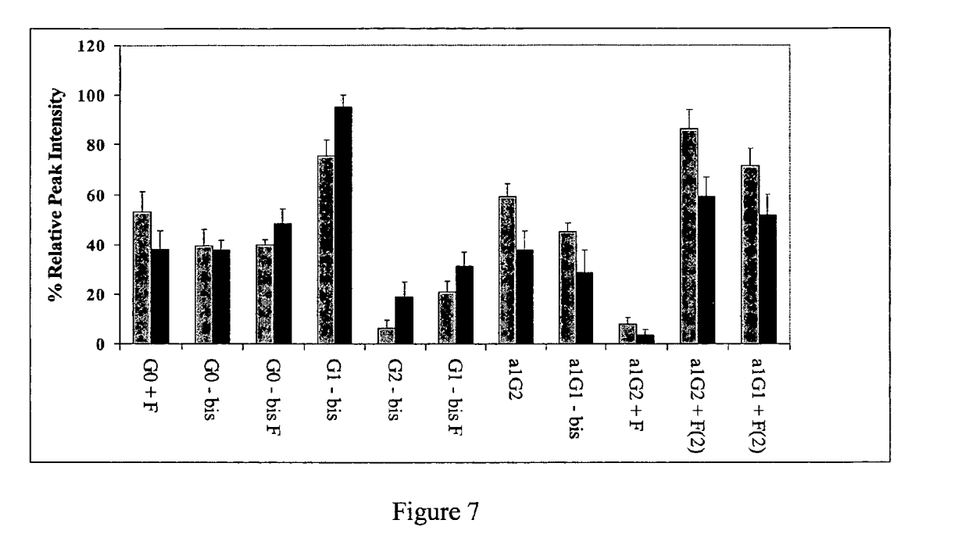
FIG. 7 A comparative analysis of the oligosaccharide moieties in RA (green bars; n=10) and healthy controls (blue, bars; n=10) using MALDI-TOF MS revealed significant ($p<0.05$) changes in the profile of at least seven species (G1bis, G2bis, G1bisF, a1G2, a1G1bis, a1G2F(2) and a1G1F (2); m/z 1420 to 2285) and indicated changes in the degree of galactosylation as well as fucosylation and sialylation.

FIG. 7 is a comparative analysis of the oligosaccharide moieties in RA (Green bars; n=10) and healthy controls (Blue bars; n=10) using MALDI-TOF MS revealed significant (p<0.05) changes in the profile of at least seven species (G1bis, G2bis, G1bisF, a1G2, a1G1bis, a1G2F(2) and a1G1F (2); m/z 1420 to 2285) and indicated changes in the degree of galactosylation as well as fucosylation and sialylation.

Figure 8:
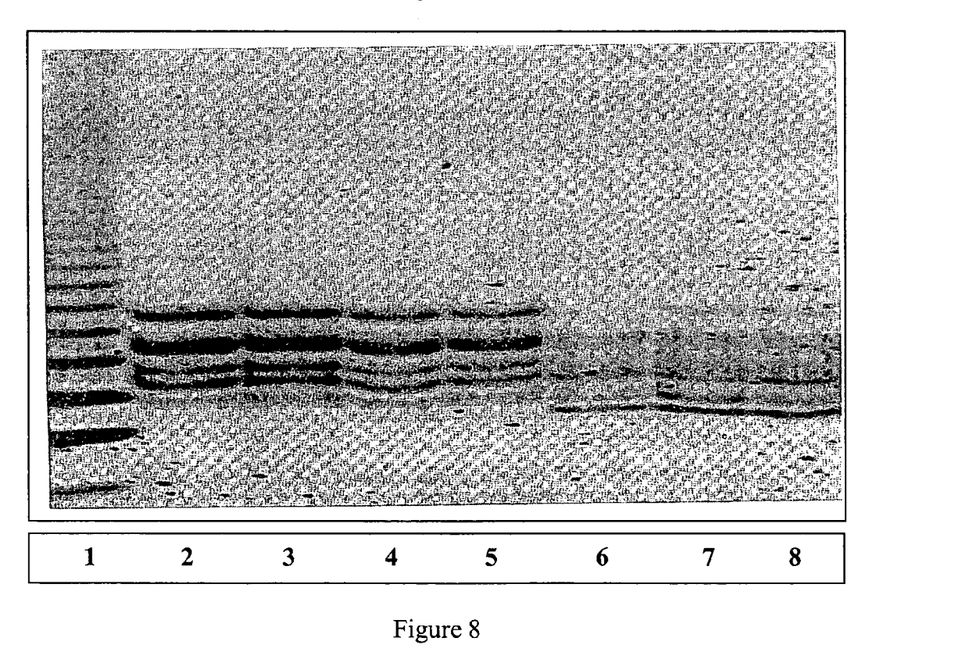
FIG. 8 Resolution of serum glycoprotein derived N-Glycans using FACE (Lane 1; homopolymer glucose ladder, Lanes 2-5; Normal healthy individuals, Lanes 6-8; RA patients).

FIG. 8 is a gel that shows the resolution of serum glycoprotein derived N-Glycans (Lane 1; Homopolymer glucose ladder, Lanes 2-5; Normal healthy individuals, Lanes 6-8; RA patients). High performance anion-exchange chromatography with pulsed amperometric detection was used to confirm these findings.

Long term Study Plans. Based on the information gathered and the techniques taught hereinabove, micro and macroscale analysis may be extended to confirm and determine the applicability of the following methods to the analysis of glycoprotein derived oligosaccharide profiles using, e.g., high density electrophoresis; HPAEC-PAD; and/or MALDI-TOF MS. These techniques were used to examine and determine the optimal conditions for using these methods to analyze the glycoprotein-derived oligosaccharide profiles in the following biological samples: Serum; Urine; and Saliva. Following confirmation of the results above, the system and method may be applied to a wide variety of bodily fluids from humans and animals, e.g., tears, spinal, fecal, etc.

With the development of easily available and optimized systems, methods, kits, techniques, etc. other patient groups may be analyzed and baseline levels determined for the individual patient or patient populations and normal populations. As such, other disease conditions may be analyzed using, e.g., serum, urine and/saliva glycoprotein samples derived oligosaccharide profiles from patients each with: Rheumatoid Arthritis. The cohort of patients (n=50) will have active disease, as assessed by a DAS and will be receiving various treatments e.g. biologics, conventional DMARDS or NSAIDS alone. Acute infection: Patients with Mycobacterium tuberculosis (n=25) infection will be compared to patients with other acute bacterial lung diseases (n=25). Healthy controls will be as follows: Normal individuals (n=50) will be randomly selected from clinics to act as healthy controls.

Inflammatory Bowel Disease: The study will be carried out at St George's Hospital, 10 patients with active UC under treatment, 10 patients who have had restorative surgery for UC, 10 patients with CD on treatment, 10 patients following resection for CD and 10 patients who had had structureplasty for active CD will be recruited to the study. In addition, 20 patients with diverticular disease will serve as controls. Patients will be recruited from the multidisciplinary IBD clinics at St George's Hospital. Post resection and restorative surgery patients will be identified from the IBD database. This will enable us to determine whether there are specific sugar bio-markers in both serum urine or and saliva from the four groups examined.

It was found that the present invention could be used to measure IgG glycosylation changes associated with rheumatoid arthritis [RA] and other rheumatic diseases has indicated the presence of sugar biomarkers that may be associated with health and disease (1, 2). Based on these earlier studies with purified Ig, the current studies are directed to extend the systems and methods to using serum, urine and saliva and to assess their direct diagnostic and prognostic potential for identifying other sugar biomarkers in a cohort of patients.

Method and Results: Studies using high density electrophoresis (FACE) indicate significant (p<0.05) differences in the profile of the following oligosaccharides: i) neutral structures, ii) monosialylated structures and iii) disialylated biantennary structures when comparing RA total serum glycoproteins with those derived from controls.

These results demonstrate that both the HPAEC-PAD and MALDI-TOF MS in addition to FACE can be used to provide rapid complete sugar profiles of serum glycoproteins and suggests that there are glycoproteins other than IgG undergoing disease specific sugar variation. These sugar print biomarkers may be useful as determinants of health and disease and may provide a relatively rapid diagnostic and prognostic test for patients presenting with arthritis.

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

REFERENCES

[1] E. Frears and J. Axford, J. Rheumatol 30. (2003) 2540-46.

[2] J. S. Axford, N. Sumar, A. Alavi, D. A. Isenberg, A. Young, K. B. Bodman and I. M. Roitt, J Clin Invest 89 (1992) 1021-31.

[3] A. Bond, A. Alavi, J. S. Axford, B. E. Bourke, F. E. Bruckner, M. A. Kerr, J. D. Maxwell, K. J. Tweed, M. J. Weldon, P. Youinou and F. C. Hay, J Autoimmun 10 (1997) 77-85.

[4] M. Watson, P. M. Rudd, M. Bland, R. A. Dwek and J. S. Axford, Arthritis Rheum 42 (1999) 1682-90.

[5] A. Alavi, N. Arden, T. D. Spector and J. S. Axford, J Rheumatol 27 (2000) 1379-85.

[6] R. Duke, G. Rook and J. Steel, GUT 31 (1990) 431-4.

[7] C. Pilkington, E. Yeung, D. Isenberg, A. K. Lefvert and G. A. Rook, Autoimmunity 22 (1995) 107-11.

[8] T. Pincus, J. Griffith, S. Pearce and D. Isenberg, Br J Rheumatol 35 (1996) 879-83.

[9] E. Filley, A. Andreoli, J. Steele, M. Waters, D. Wagner, D. Nelson, K. Tung, T. Rademacher, R. Dwek and G. A. Rook, Clin Exp Immunol 76 (1989) 343-7.

[10] J. Axford, N. Sumar and K. Bodman, Arthritis Rheum 33 (1990) 85.

[11] R. Hernandez-Pando, P. Reyes, C. Espitia, Y. Wang, G. Rook and R. Mancilla, J Rheumatol 21 (1994) 1870-6.

[12] J. McCulloch, Y. W. Zhang, M. Dawson, G. D. Harkiss, E. Peterhans, H. R. Vogt, P. M. Lydyard and G. A. Rook, Rheumatol Int 14 (1995) 243-8.

[13] R. Rocklin and C. Pohl, J. Liq. Chromatogr 6 (1983) 1577-1590.

[14] J. Vliegenthart, Pure Appl. Chem 53 (1981) 45-77.

[15] R. Craig and A. Atkinson, Jr. Gastroenterology 95 (1988) 223-231.

[16] B. Griffin and G. Williams, Biomed. Chromatogr 4 (1990) 87-88.

[17] A. Alavi and e. al, Br J Rheumatol 30 (1996) 2540-6.

[18] R. Dawson, D. Elliott, W. Elliott and K. Jones, 3rd edition ed., Oxford University Press, New York, 1986.

What is claimed is:

1. A diagnostic method comprising:
    comparing a biosugar profile of a biological sample of a patient suspected of having a disease associated with changes in the biosugar profile to a healthy biosugar profile from the same type of biological sample; and
    providing the patient with a formulation that provides nutritionally effective amounts of one or more sugars to modify the biosugar profile of the patient.

2. The method of claim 1, wherein the biological sample is a serum, a blood, a plasma, a urine, a saliva, a peritoneal, a stool, a mucus, a tear, a sweat, a biopsy, a sperm or a cerebrospinal fluid sample.

3. The method of claim 1, wherein the patient is suspected of having an auto-inflammatory disease, an auto-immune disease, a metabolic disease, a neurological disease, an infectious disease or combinations thereof.

4. The method of claim 1, wherein the biosugar profile is determined using high density electrophoresis, high performance anion-exchange chromatography (HPAEC), high performance anion-exchange chromatography pulsed amperometric detection (HPAEC-PAD), matrix-assisted laser desorption/ionization mass spectroscopy (MALDI), matrix-assisted laser desorption/ionization mass spectroscopy time of flight (MALDI-TOF), matrix-assisted laser desorption/ionization mass spectroscopy time of flight—mass spectrometry (MALDI-TOF MS), enzyme-linked immunosorbent assay or combinations thereof.

5. The method of claim 1, further comprising the step of supplementing the diet of the patient with a nutritionally effective amount of one or more saccharides selected from galactose, galactosamine, glucosamine, glucose, mannose, acetylated-mannose, N-acetylneuraminic acid, fucose, N-acetylgalactosamine, N-acetylglucosamine, xylose and mixtures or combinations thereof based on the biosugar profile.

6. The method of claim 1, further comprising the step of supplementing the diet of the patient with a nutritionally effective amount of one or more saccharides obtained from gum tragacanth, guar gum, grain flour, rice flour, sugar cane, beet sugar, potato, milk, agar, algin, locust bean gum, psyllium, karaya gum, seed gums, Larch tree extract, aloe vera extract, gum ghatti, starch, cellulose, degraded cellulose, fructose, high fructose corn syrup, pectin, chitin, acacia, gum arabic, alginic acid, carrageenan, dextran, xanthan gum, chondroitin sulfate, sucrose, acetylated polymannose, maltose, glucan, lentinan, mannan, levan, hemicellulose, inulin, fructan, lactose, and one or more anti-oxidants and combinations thereof.

7. The method of claim 1, further comprising the step of supplementing the diet of the patient with one or more nutritional supplements selected from anti-oxidants, vitamins, minerals, amino acids, nucleic acids, saccharides, herbal extracts, mixtures and combinations thereof.

8. The method of claim 1, further comprising the step of administering to the patient a nutritionally effective amount of a formulation that modifies the biosugar profile orally, intravenously, intramuscularly, intraperitoneally, subcutaneously, by intranasal instillation, by application to mucous membranes, or by instillation into hollow organ walls or newly vascularized blood vessels.

9. The method of claim 1, wherein the patient is suspected to having an inflammatory disease selected from the group consisting of transplantation rejection, nephritis, asthma, respiratory distress syndrome, gastritis, rheumatoid diseases, sepsis, thrombosis, autoimmune diseases, and coronary disease.

10. The method of claim 1, wherein the patient is suspected to having a transplantation rejection, a renal allograft rejection, a cardiac allograft rejection, a transplantation-associated vasculopathy, a nephritis, an acute glomerulonephritis, lupus nephritis, and tubulointerstitial nephritis, an asthma, an allergic asthma, a respiratory distress syndrome, a gastritis, a rheumatoid disease selected from the group consisting of lupus and arthritis, a vasculitis, a diabetes, a sepsis, a thrombosis, a coronary artery disease selected from the group consisting of restenosis after angioplasty, restenosis after by-pass surgery, ischemia or an inflammatory bowel disease.

11. A method for determining a deficiency in one or more essential saccharides comprising the steps of:
    obtaining a biological sample from a mammal suspected of having a deficiency in one or more essential saccharides; and
    determining a biosugar profile of the biological sample;
    determining a deficiency in one or more essential saccharides; and
    designing a formulation that provides nutritionally effective amounts of one or more saccharides in amounts sufficient to modify the biosugar profile of the patient.

12. The method of claim 11, wherein the deficiency in the one or more essential saccharides is determined and an essential sugar supplement is designed to modify the biosugar profile.

13. The method of claim 11, wherein the biological sample is a serum, a blood, a plasma, a urine, a saliva, a peritoneal, a stool, a mucus, a tear, a sweat, a biopsy or a cerebrospinal fluid sample.

14. The method of claim 11, wherein the mammal is suspected of having an auto-inflammatory disease, an auto-immune disease, a metabolic disease, an infectious disease or combinations thereof.

15. The method of claim 11, wherein the biosugar profile is determined using high density electrophoresis, high performance anion-exchange chromatography (HPAEC), high performance anion-exchange chromatography pulsed amperometric detection (HPAEC-PAD), matrix-assisted laser desorption/ionization mass spectroscopy (MALDI), matrix-assisted laser desorption/ionization mass spectroscopy time of flight (MALDI-TOF), matrix-assisted laser desorption/ionization mass spectroscopy time of flight—mass spectrometry (MALDI-TOF MS), enzyme-linked immunosorbent assay or combinations thereof.

16. The method of claim 11, further comprising the step of supplementing the diet of the mammal with one or more saccharides selected from galactose, galactosamine, glucosamine, glucose, mannose, acetylated-mannose, N-acetylneuraminic acid, fucose, N-acetylgalactosamine, N-acetylglucosamine, xylose and mixtures or combinations thereof based on the biosugar profile.

17. The method of claim 11, further comprising the step of supplementing the diet of the mammal with one or more saccharides obtained from gum tragacanth, guar gum, grain flour, rice flour, sugar cane, beet sugar, potato, milk, agar, algin, locust bean gum, psyllium, karaya gum, seed gums, Larch tree extract, aloe vera extract, gum ghatti, starch, cellulose, degraded cellulose, fructose, high fructose corn syrup, pectin, chitin, acacia, gum arabic, alginic acid, carrageenan, dextran, xanthan gum, chondroitin sulfate, sucrose, acetylated polymannose, maltose, glucan, lentinan, mannan, levan, hemicellulose, inulin, fructan, lactose and mixtures or combinations thereof.

18. The method of claim 11, further comprising the step of administering to the mammal a nutritionally effective amount of a formulation orally, intravenously, intramuscularly, intraperitoneally, subcutaneously, by intranasal instillation, by application to mucous membranes, or by instillation into hollow organ walls or newly vascularized blood vessels or a combination thereof, wherein the biosugar profile is modified.

19. The method of claim 11, wherein the mammal is suspected to having an inflammatory disease selected from the group consisting of transplantation rejection, nephritis, asthma, respiratory distress syndrome, gastritis, rheumatoid diseases, sepsis, thrombosis, autoimmune diseases and coronary disease.

20. The method of claim 11, wherein the mammal is suspected to having a transplantation rejection, a renal allograft rejection, a cardiac allograft rejection, a transplantation-associated vasculopathy, a nephritis, an acute glomerulonephritis, lupus nephritis, and tubulointerstitial nephritis, an asthma, an allergic asthma, a respiratory distress syndrome, a gastritis, a rheumatoid disease selected from the group consisting of lupus and arthritis, a vasculitis, a diabetes, a sepsis, a thrombosis, a coronary artery disease selected from the group consisting of restenosis after angioplasty, restenosis after bypass surgery, ischemia or an inflammatory bowel disease.

* * * * *